United States Patent
Herrmann

(10) Patent No.: US 8,388,677 B2
(45) Date of Patent: Mar. 5, 2013

(54) ANTI-THROMBOGENIC AND ANTI-RESTENOTIC VASCULAR MEDICAL DEVICES

(75) Inventor: Robert A. Herrmann, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1399 days.

(21) Appl. No.: 10/977,695

(22) Filed: Oct. 29, 2004

(65) Prior Publication Data

US 2006/0095120 A1  May 4, 2006

(51) Int. Cl.
*A61F 2/06* (2006.01)
(52) U.S. Cl. ...................................... 623/1.42
(58) Field of Classification Search ................. 623/1.15, 623/1.42–1.44
See application file for complete search history.

(56) References Cited

U.S. PATENT DOCUMENTS

| | | | | |
|---|---|---|---|---|
| 5,733,925 | A | 3/1998 | Kunz et al. | 514/449 |
| 6,545,097 | B2 | 4/2003 | Pinchuk et al. | 525/240 |
| 6,706,274 | B2 | 3/2004 | Herrmann et al. | 424/423 |
| 6,780,849 | B2 | 8/2004 | Herrmann et al. | 514/23 |
| 2002/0107330 | A1* | 8/2002 | Pinchuk et al. | 525/242 |
| 2004/0002755 | A1 | 1/2004 | Fischell et al. | 623/1.42 |
| 2005/0220835 | A1* | 10/2005 | Jayaraman et al. | 424/423 |

FOREIGN PATENT DOCUMENTS

| | | |
|---|---|---|
| JP | 2004097810 | 2/2004 |
| JP | 2004-267283 | 9/2004 |
| WO | WO 03/090684 A2 | 11/2003 |
| WO | 2006023693 A2 | 3/2006 |

OTHER PUBLICATIONS

Roberts, Campbell D.K., MD, "Optimal Stent Design for Drug Delivery," Reviews in Cardiovascular Medicine, vol. 5, Suppl. 2, 2004, S9-S15.
Drug Eluting Stents, http://biomed.brown.edu/Courses/B1108/B1108_2004_Groups/Group05/Drug%20Eluting%20Stents/drugs_and_pharmacokinetics.htm, copyright 2004, exact date unknown but before the filed of the instant application, 3 pages.

* cited by examiner

*Primary Examiner* — Melanie Tyson
(74) *Attorney, Agent, or Firm* — Mayer & Williams PC; David B. Bonham; Keum J. Park

(57) ABSTRACT

A medical device is provided which is adapted for implantation or insertion into the vasculature. The medical device has (a) a medical device substrate; (b) a lower polymeric layer, provided over the substrate made of a nitric oxide donor and a polymer; and (c) an upper polymeric layer, provided over the lower polymer layer, made of a polymer and an anti-restenotic agent.

27 Claims, 2 Drawing Sheets

ANTI-THROMBOGENIC AND ANTI-RESTENOTIC VASCULAR MEDICAL DEVICES

TECHNICAL FIELD

This invention relates to medical devices for drug delivery, and more particularly to vascular medical devices for the delivery of nitric oxide and anti-restenotic agents.

BACKGROUND OF THE INVENTION

Restenosis is a problem that commonly occurs following angioplasty or stent placement in the vasculature. Currently, several vascular stents are commercially available, which are coated with a drug releasing matrix containing an anti-restenotic drug. Paclitaxel is an example of an effective drug for reducing the occurrence of clinical restenosis and is currently available from Boston Scientific Corporation within the TAXUS™ Express²™ Paclitaxel-Eluting Coronary Stent System.

With the use of paclitaxel or other anti-restenotic drugs, there can be a delay in vascular re-endothelialization, which can lead to thrombosis unless appropriate preventative steps are taken. Consequently, patients receiving drug eluting stents are typically provided with systemic anti-platelet therapy for at least 6 months following stent implantation. Like all drugs, anti-platelet agents have side effects. Moreover, additional costs are added onto the therapy.

Accordingly, it would be desirable to provide a drug eluting stent, which would reduce or eliminate the requirement for systemic anti-platelet therapy.

SUMMARY OF THE INVENTION

The above and other challenges are addressed by the present invention.

In accordance with one aspect of the present invention, a medical device is provided, which is adapted for implantation or insertion into the vasculature, and which comprises the following: (a) a medical device substrate; (b) a lower polymeric layer provided over the substrate, which lower layer comprises a nitric oxide donor and a polymer; and (c) an upper polymeric layer provided over the lower polymer layer, which upper polymeric layer comprises a polymer and an anti-restenotic agent.

An advantage of the present invention is that by adding nitric oxide as an anti-thrombotic agent to vascular medical devices, such as stents, the requirement of systemic anti-platelet therapy is reduced or eliminated.

Moreover, nitric oxide is a ubiquitous molecule, produced by many cell types in the body, making it likely to be well tolerated in clinical trials and to have a variety of beneficial effects beyond its role as an anti-thrombotic agent. For example, it is known that the endothelium produces nitric oxide, which acts as a smooth muscle cell relaxant (affecting the tone of the vessel wall) and as an anti-white blood cell agent, in addition to acting as an anti-thrombotic agent. Nitric oxide may also aid in vascular re-endothelialization.

The above and many other embodiments and advantages of the present invention will become immediately apparent to those of ordinary skill in the art upon review of the Detailed Description and Claims to follow.

DETAILED DESCRIPTION

Figure 1:
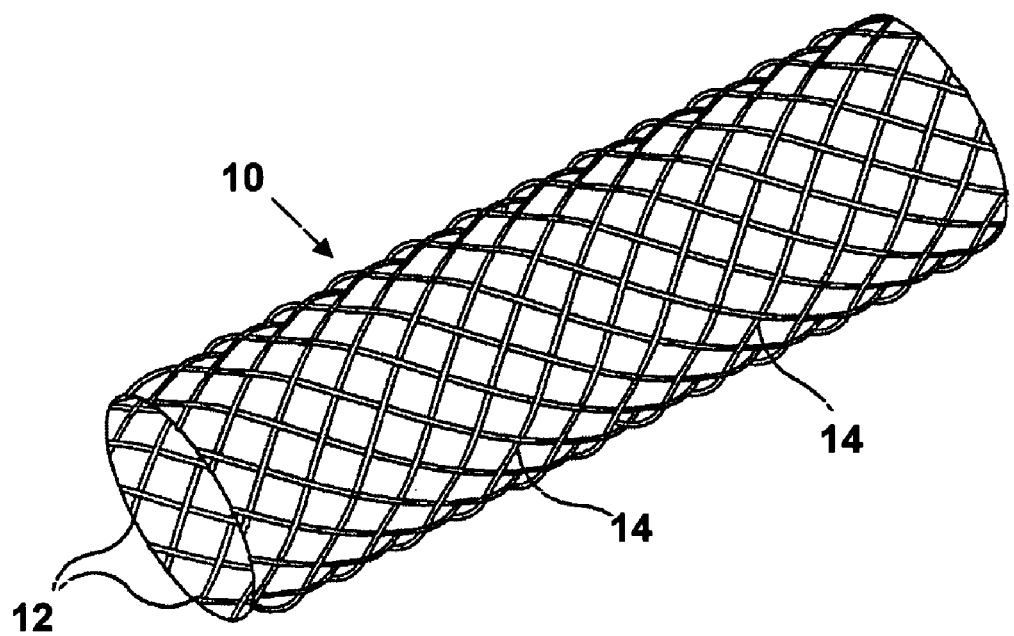
FIG. 1 is a schematic longitudinal perspective view of a braided stent in accordance with an embodiment of the present invention.

According to an aspect of the present invention, implantable or insertable devices are provided, which comprise the following: (a) a medical device substrate; (b) a lower polymeric layer, provided over at least a portion of the substrate, which contains at least one polymer and at least one nitric oxide donor; and (c) an upper polymeric layer, provided over at least a portion of the lower layer, which contains at least one polymer and at least one anti-restenotic agent.

Materials suitable for use in the underlying medical device substrates include metallic, ceramic, and polymeric substrate materials. The substrate material can also be a semiconductor (e.g., silicon or carbon). Suitable metals can be selected, for example, from the following: substantially pure metals (e.g., silver, gold, platinum, palladium, iridium, osmium, rhodium, titanium, tungsten, and ruthenium) and metal alloys such as cobalt-chromium alloys, nickel-titanium alloys (e.g., nitinol), cobalt-chromium-iron alloys (e.g., elgiloy alloys), nickel-chromium alloys (e.g., inconel alloys), and iron-chromium alloys (e.g., stainless steels, which contain at least 50% iron and at least 11.5% chromium). Suitable ceramic materials can be selected, for example, from the following: silica- and/or calcium-phosphate-based glasses, sometimes referred to as glass ceramics (e.g., silica and bioglass); calcium phosphate ceramics (e.g., hydroxyapatite); metal oxides, including aluminum oxides and transition metal oxides (e.g., oxides of titanium, zirconium, hafnium, tantalum, molybdenum, tungsten, rhenium and iridium); and carbon based ceramic-like materials such as silicon carbides and carbon nitrides. Polymeric materials suitable for use as medical device substrates can be selected, for example, from the polymers set forth further below.

As noted above, disposed over at least a portion of the substrate is a lower polymeric layer, which contains at least one polymer and at least one nitric oxide donor. As used herein, a "polymeric layer" is a layer that contains one or more polymers, which make up 50 wt % or more of the layer, typically 75% or more, 90% or more, or even 95% or more of the layer in some instances. As used herein a "layer" of a given material is a region of that material whose thickness is small compared to both its length and width. Terms such as "film," "layer" and "coating" may be used interchangeably herein. A layer need not be planar, for example, taking on the contours of an underlying substrate. A layer can be discontinuous (e.g., patterned). Hence, the lower polymeric layer can cover the entirety of the substrate, or it can cover only a portion of the substrate, in which case it can be provided at a variety of locations, and in a variety of shapes.

As also noted above, disposed over at least a portion of the lower layer is an upper polymeric layer, which contains at least one polymer and at least one anti-restenotic agent. The upper polymeric layer can cover the entirety of the lower polymeric layer, or it can cover only a portion thereof. Moreover, while the upper polymeric layer is disposed over at least a portion of the lower layer, the lower layer need not intervene between the upper polymeric layer and the medical device substrate at all locations.

The upper and lower polymeric layers of the present invention can be formed over the medical device substrate; or they can be pre-formed and attached to an underlying medical device substrate.

As noted above, the lower and upper polymeric layers each contain one or more polymers. The polymers within the lower and upper polymeric layers may be the same or different.

As used herein, "polymers" are molecules containing one or more chains, each containing multiple copies of one or more constitutional units. An example of a common polymer is polystyrene

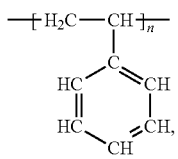

where n is an integer, typically an integer of 10 or more, more typically on the order of 10's, 100's, 1000's or even more, in which the chain contains styrene monomers:

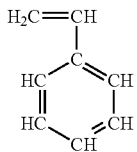

(i.e., the chain originates from, or has the appearance of originating from, the polymerization of styrene monomers, in this case, the addition polymerization of styrene monomers). As used herein, "copolymers" are polymers that contain at least two dissimilar constitutional units and include random, statistical, gradient, periodic and block copolymers.

Polymers for use in the polymeric layers of the invention can take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

The polymeric layers of the invention can be formed from a variety of polymers. The specific polymer or polymers selected will depend on a variety of factors, including the biocompatibility of the polymer, the compatibility between the polymer and the drug that is to be loaded within the polymeric layer, the desired release kinetics for the drug, and so forth.

For example, suitable polymers for use in the polymeric layers of the present invention can be selected include the following: (a) homopolymers and copolymers consisting of or containing one or more acrylic acid monomers such as the following: acrylic acid and its salt forms (e.g., potassium acrylate and sodium acrylate); acrylic acid anhydride; acrylic acid esters including alkyl acrylates (e.g., methyl acrylate, ethyl acrylate, propyl acrylate, isopropyl acrylate, butyl acrylate, sec-butyl acrylate, isobutyl acrylate, tert-butyl acrylate, hexyl acrylate, cyclohexyl acrylate, isobornyl acrylate, 2-ethylhexyl acrylate, dodecyl acrylate and hexadecyl acrylate), arylalkyl acrylates (e.g., benzyl acrylate), alkoxyalkyl acrylates (e.g., 2-ethoxyethyl acrylate and 2-methoxyethyl acrylate), halo-alkyl acrylates (e.g., 2,2,2-trifluoroethyl acrylate) and cyano-alkyl acrylates (e.g., 2-cyanoethyl acrylate); acrylic acid amides (e.g., acrylamide, N-isopropylacrylamide and N,N dimethylacrylamide); and other acrylic-acid derivatives (e.g., acrylonitrile); (b) homopolymers and copolymers consisting of or containing one or more methacrylic acid based monomers such as the following: methacrylic acid and its salts (e.g., sodium methacrylate); methacrylic acid anhydride; methacrylic acid esters (methacrylates) including alkyl methacrylates (e.g., methyl methacrylate, ethyl methacrylate, isopropyl methacrylate, butyl methacrylate, isobutyl methacrylate, t-butyl methacrylate, hexyl methacrylate, cyclohexyl methacrylate, 2-ethylhexyl methacrylate, octyl methacrylate, dodecyl methacrylate, hexadecyl methacrylate, octadecyl methacrylate, aromatic methacrylates (e.g., phenyl methacrylate and benzyl methacrylate), hydroxyalkyl methacrylates (e.g., 2-hydroxyethyl methacrylate and 2-hydroxypropyl methacrylate), aminoalkyl methacrylates (e.g., diethylaminoethyl methacrylate and 2-tert-butyl-aminoethyl methacrylate), additional methacrylates (e.g., isobornyl methacrylate and trimethylsilyl methacrylate); and other methacrylic-acid derivatives (e.g., methacrylonitrile); (c) homopolymers and copolymers consisting of or containing one or more vinyl aromatic monomers (i.e., those having aromatic and vinyl moieties) such as the following: unsubstituted vinyl aromatics (e.g., styrene and 2-vinyl naphthalene); vinyl substituted aromatics (e.g., ac-methyl styrene); and ring-substituted vinyl aromatics including ring-alkylated vinyl aromatics (e.g., 3-methylstyrene, 4-methylstyrene, 2,4-dimethylstyrene, 2,5-dimethylstyrene, 3,5-dimethylstyrene, 2,4,6-trimethylstyrene, and 4-tert-butylstyrene), ring-alkoxylated vinyl aromatics (e.g., 4-methoxystyrene and 4-ethoxystyrene), ring-halogenated vinyl aromatics (e.g., 2-chlorostyrene, 3-chlorostyrene, 4-chlorostyrene, 2,6-dichlorostyrene, 4-bromostyrene and 4-fluorostyrene) and ring-ester-substituted vinyl aromatics (e.g., 4-acetoxystyrene); (d) homopolymers and copolymers consisting of or containing one or more vinyl monomers (beyond the above vinyl aromatic monomers) such as the following: vinyl alcohol; vinyl esters (e.g., vinyl benzoate, vinyl 4-tert-butyl benzoate, vinyl cyclohexanoate, vinyl pivalate, vinyl trifluoroacetate and vinyl butyral); vinyl amines (e.g., 2-vinyl pyridine, 4-vinyl pyridine, and vinyl carbazole); vinyl halides (e.g., vinyl chloride and vinyl fluoride); alkyl vinyl ethers (e.g., methyl vinyl ether, ethyl vinyl ether, propyl vinyl ether, butyl vinyl ether, isobutyl vinyl ether, 2-ethylhexyl vinyl ether, dodecyl vinyl ether, tert-butyl vinyl ether and cyclohexyl vinyl ether); and other vinyl compounds (e.g., 1-vinyl-2-pyrrolidone and vinyl ferrocene); (e) homopolymers and copolymers consisting of or containing one or more aromatic monomers (beyond the above vinyl aromatic monomers) such as acenaphthalene and indene; (f) homopolymers and copolymers consisting of or containing one or more cyclic ether monomers such as the following: tetrahydrofuran, trimethylene oxide, methyl glycidyl ether, butyl glycidyl ether, allyl glycidyl ether, epibromohydrin, epichlorohydrin, 1,2-epoxybutane, 1,2-epoxyoctane and 1,2-epoxydecane; (g) homopolymers and copolymers consisting of or containing one or more ester monomers (beyond those ester monomers listed above) such as ethylene malonate, vinyl acetate and vinyl propionate; (h) homopolymers and copolymers consisting of or containing one or more alkene monomers such as the following: unsubstituted alkene monomers (e.g., ethylene, propylene, isobutylene, 1-butene, trans-butadiene, 4-methyl pentene, 1-octene, 1-octadecene, and other α-olefins, as well as cis-isoprene and trans-isoprene) and halogenated alkene monomers (e.g., vinylidene chloride, vinylidene fluoride, cis-chlorobutadiene, trans-chlorobutadiene, and tetrafluoroethylene); and (i) homopolymers and copolymers consisting of or containing one or more organo-siloxane monomers such as dimethylsiloxane, diethylsiloxane, methylethylsiloxane, methylphenylsiloxane and diphenylsiloxane.

As further examples, suitable polymers for use in the polymeric layers of the present invention, which are not necessarily exclusive of the above examples, can be selected include the following: polyolefins such as polyethylenes, polypropylenes, and polybutylenes, polyolefin copolymers, e.g., ethylenic copolymers such as ethylene vinyl acetate (EVA) copolymers, ethylene-methacrylic acid copolymers and ethylene-acrylic acid copolymers where some of the acid groups can be neutralized, e.g., with zinc or sodium ions (commonly known as ionomers); vinyl aromatic polymers such as polystyrene; vinyl aromatic copolymers such as styrene-ethylene-butylene copolymers (e.g., a polystyrene-polyethylene/butylene-polystyrene (SEBS) copolymer, available as Kraton® G series polymers), styrene-isobutylene copolymers (e.g., polystyrene-polyisobutylene-polystyrene (SIBS) copolymers such as those disclosed in U.S. Pat. No. 6,545,097 to Pinchuk), butadiene-styrene copolymers, and styrene-maleic acid (SMA) copolymers (e.g., random copolymers of styrene and maleic anhydride, such as those available from Nova Chemical, and alternating copolymers of styrene and maleic anhydride, such as those available from Scientific Polymer Products, Inc.); polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA); silicones; polycarbonates; thermoplastic polyurethanes (TPU); and elastomeric polyurethanes and polyurethane copolymers (including block and random copolymers that are polyether based, polyester based, polycarbonate based, aliphatic based, aromatic based and mixtures thereof; examples of commercially available polyurethane copolymers include Carbothane®, Tecoflex®, Tecothane®, Tecophilic®, Tecoplast®, Pellethane®, Chronothane® and Chronoflex®).

As noted above, in addition to at least one polymer, the upper polymeric layer of the medical devices of the present invention contains at least one anti-restenotic agent, while the lower polymeric layer contains at least one nitric oxide donor. The anti-restenotic agent is included to treat restenosis. (As used herein, "treatment" refers to the prevention of a disease or condition, the reduction or elimination of symptoms associated with a disease or condition, or the substantial or complete elimination of a disease or condition.) The nitric oxide donor is included to provide an anti-thrombogenic surface for the medical device, although it can have other desirable effects including reduced white blood cell adhesion.

Generically, the anti-restenotic agents and the nitric oxide donors may be referred to herein as "drugs," "agents," "therapeutic agents," "pharmaceutically active agents," "pharmaceutically active materials," and other related terms.

A wide range of anti-restenotic agent(s) and nitric oxide donor(s) loadings can be used in connection with the medical devices of the present invention, with the therapeutically effective amounts being readily determined by those of ordinary skill in the art and ultimately depending, for example, upon the age, sex and condition of the patient, the nature of the therapeutic agent, the nature of the polymeric layer(s), the nature of the medical device, and so forth.

The release profile associated with each of the polymeric layers of the present invention can be modified in a number of ways, including changing the composition and molecular weight of the polymers that are used in the polymeric layers, changing the thickness of the layers, and so forth.

Numerous therapeutic agents have been identified as candidates for treatment of restenosis. Suitable anti-restenotic agents useful for the practice of the present invention can be selected, for example, from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) blood rheology modulators such as pentoxifylline, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguaiaretic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilones, Epo D), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, (cc) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (dd) Ace inhibitors and B-blockers, (ee) Barkct inhibitors, (if) phospholamban inhibitors, and (gg) Serca 2 gene/protein.

Numerous additional therapeutic agents useful for the practice of the present invention are also disclosed in U.S. Pat. No. 5,733,925 assigned to NeoRx Corporation, the entire disclosure of which is incorporated by reference.

Thus suitable anti-restenotic agents for use in the present invention can be selected from a variety of agents, including, for example, anti-neoplastic agents, antiproliferative agents, anti-mitotic agents, immunomodulators, migration inhibitors, ECM-modulators, and agents that promote healing and endothelialization, among others.

Some particularly beneficial anti-restenotic agents suitable for the present invention can be selected from the following: sirolimus, tacrolimus, everolimus, cyclosporine, natural and synthetic corticosteroids such as dexamethasone, M-prednisolone, leflunomide, mycophenolic acid, mizoribine, tranilast, biorest, estradiol, statins, paclitaxel, Epo D, actinomycin (e.g., actinomycin D), geldanamycin, cilostazole, methotrexate, angiopeptin, vincristine, mitomycin, QP-2, C-MYC antisense, ABT-578 (Abbott Laboratories), restenASE, choloro-deoxyadenosine, PCNA Ribozyme, batimastat, prolyl hydroxylase inhibitors, halofuginone, C-proteinase inhibitors, probucol, trapidil, liprostin, Resten-NG, Ap-17, abciximab, clopidogrel and ridogrel, among others.

"Nitric oxide donor compound" means any compound (including small molecules, polymers, etc.) that releases nitric oxide or which acts as a substrate leading to the formation of nitric oxide. A wide variety of nitric oxide donor compounds are available for the release/production of nitric oxide, including the following: (a) organic nitrates (i.e., organic compounds having C—O—NO$_2$ groups); examples include nitroglycerine; (b) O-nitrosylated compounds (i.e., compounds, preferably organic, having —O—NO groups) (these are also known as O-nitroso compounds or in some cases organic nitrites); (c) S-nitrosylated compounds (i.e., compounds, preferably organic, having an —S—NO group) (these are also known as S-nitroso compounds or S-nitrosothiol compounds); examples include glutathione, S-nitrosylated derivatives of captopril, S-nitrosylated-proteins/peptides, S-nitrosylated oligosaccharides and polysaccharides, and so forth; (d) nonoate compounds (i.e., compounds having at least one

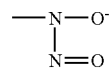

group); examples include substituted piperazines

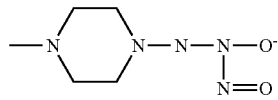

and diazeniumdiolates; (e) inorganic nitroso compounds (i.e., inorganic compounds having —NO groups); examples include sodium nitroprusside; (f) sydnonimines; and (g) L-arginine (which does not release NO directly, but rather is an enzyme substrate which leads to the formation of nitric oxide in vivo).

Without wishing to be bound by theory, it is believed that nitric oxide can be generated at the surface of the medical devices of the present invention by various mechanisms. As a specific example, a donor compound may be selected that does not substantially release/produce nitric oxide until contact is made with tissue outside of the medical device (a specific example is L-arginine, which acts as an enzyme substrate for the formation of nitric oxide within vascular tissue, such as the endothelium). In such instances, production of nitric oxide can be manipulated by controlling the rate at which the nitric oxide donor compound is released from the medical device, for example, by mass transport, either with or without the assistance of solvent (e.g., bodily fluids), from the underlying polymeric layer and through the overlying polymeric layer. As another specific example, a donor compound may be selected that does not substantially release/produce nitric oxide until contact is made with solvent (e.g., bodily fluids). In these instances, the release/production of nitric oxide can be manipulated, for example, by controlling the rate at which the donor compound is released from medical device (see above), if solvent contact is made outside the device, or if contact between the solvent and donor compound is made within the medical device, by controlling one or more of the following: (i) the rate at which the donor compound is transported toward the surface of the device, (ii) the rate at which the which solvent is conveyed into the polymeric layer(s) from the surface and (iii) the rate at which the nitric oxide, once formed, is transported through the polymeric layer(s) to the device surface.

Because platelet generation and cell adhesion are surface phenomena that occur relatively shortly after medical device introduction, it is ordinarily considered desirable to place agents for reduction of platelet generation and cell adhesion in the outer layer of the device. However, in the present invention, the layer containing the nitric oxide donor is placed beneath the layer containing the anti-restenotic agent. This is desirable, because nitric oxide donors (and their nitric oxide products) are commonly more readily released from polymeric layers than are anti-restenotic agents, for example, due to differences in molecular weight and differences in hydrophilicity, and so forth. Moreover, it is desirable to have a slow steady release of the nitric oxide donor and/or its products to maintain an anti-thrombogenic surface until normal endothelium has healed over the medical device. Slow and steady release is facilitated by providing an upper polymeric layer over the nitric-oxide-donor-containing polymeric layer. In addition to providing release modulation for the nitric oxide donor, this overlying polymeric layer also provides release modulation of the anti-restenotic agent. Consequently, one aspect of the novelty of the present invention is that the drug for which immediate delivery is typically desired (i.e., the nitric oxide donor) is placed in a layer beneath the layer that contains the drug for which longer term delivery is typically desired (i.e., the anti-restenotic drug).

Of course, the medical devices in accordance with the present invention can include additional layers other than those specifically described herein, including one or more layers disposed between the medical device substrate and the lower polymeric layer (e.g., a buffer layer, etc.), one or more layers disposed between the lower polymeric layer and the upper polymeric layer (e.g., a barrier layer, etc.), and one or more layers disposed over the upper polymeric layer (e.g., a barrier layer, a hydrogel layer, etc.).

Examples of medical devices suitable for use in conjunction with the present invention include a variety of medical devices that are adapted for insertion into or implantation within the vasculature. Specific medical devices can be selected, for example, from the following: vascular catheters, vascular stents, guide wires, balloons, filters (e.g., vena cava filters), vascular grafts, stent grafts, cerebral aneurysm filler coils (including Guglilmi detachable coils and metal coils), myocardial plugs, vascular patches, pacemakers and pacemaker leads, heart valves, vascular valves, vascular tissue engineering scaffolds, sutures, suture anchors, anastomosis clips and rings, tissue staples and ligating clips at surgical sites as well as various other coated substrates that are implanted or inserted into the vasculature.

Preferred subjects (also referred to as "patients") for introduction of the medical devices of the invention are vertebrate subjects, more preferably mammalian subjects and even more preferably human subjects.

A specific example of a medical device for use in conjunction with the present invention is a vascular stent which is inserted or implanted into a blood vessel, for example, into a coronary artery after a procedure such as percutaneous transluminal coronary angioplasty ("PCTA"). Such stents are used to maintain the patency of the coronary artery by supporting the arterial walls and preventing abrupt reclosure or collapse thereof which can occur after PCTA.

Figure 2:
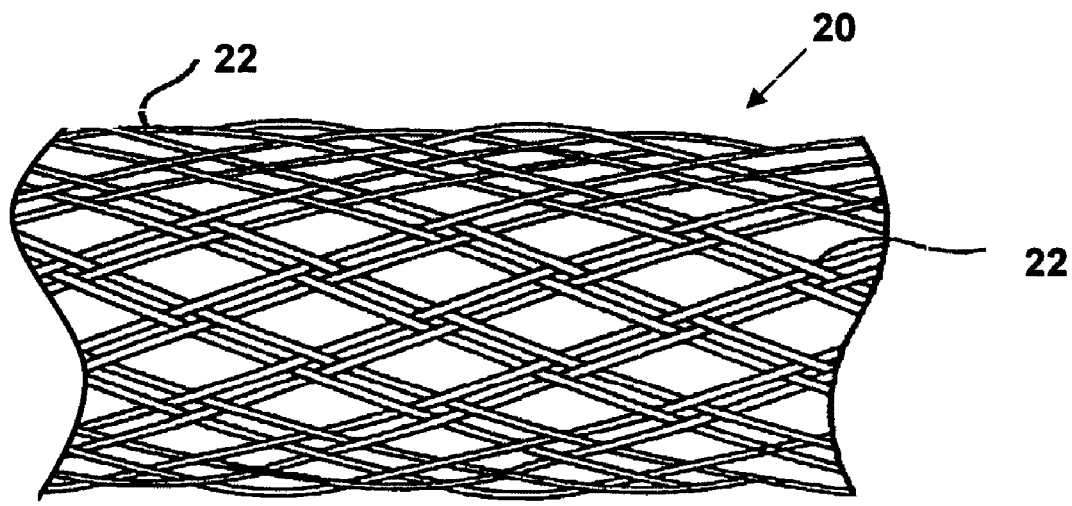
FIG. 2 is a schematic partial side view of braided stent in accordance with another embodiment of the present invention.
Figure 3:
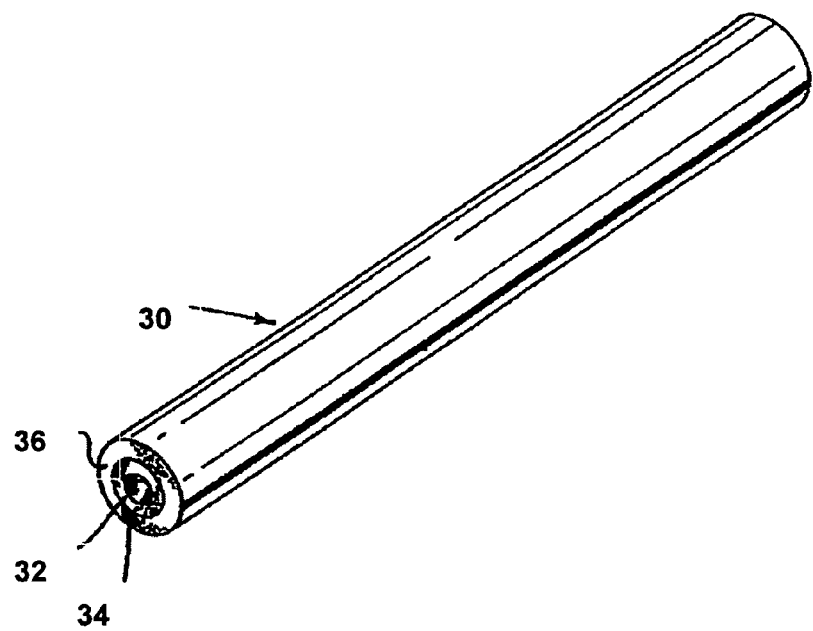
FIG. 3 is a schematic, partial longitudinal view showing a coated metallic filament used in the stents of FIG. 1 or of FIG. 2, in accordance with an embodiment of the present invention.

One specific embodiment of a stent in accordance with the present invention is illustrated schematically in FIG. 1. Referring now to FIG. 1, a stent 10 is shown, which is formed from oppositely-directed, parallel, spaced-apart and helically wound filaments 12. The filaments 12 are interwoven and form intersecting points 14, providing an open mesh or braided construction. FIG. 2 shows a stent 20 of similar design, formed from trios of oppositely-directed, parallel, spaced-apart and helically wound filaments 22. Hence, the oppositely-directed helical filaments can comprise one (as shown in FIG. 1), or a plurality (as shown in FIG. 2) of individual metallic filaments. Such metallic filaments may comprise the same or different materials. FIG. 3 show a coated metallic filament 30, a plurality of one or more of which may be knitted, wound or woven in the form of a stent in accordance with the present invention, such as the stents illustrated in FIGS. 1 and 2. The coated metallic filament 30 shown comprises a metallic core 32 which acts as a substrate for a lower polymeric layer 34 (which contains at least one polymer and at least one nitric oxide donor) and an upper polymeric layer 36 (which contains at least one polymer and an anti-restenotic agent).

Figure 4:
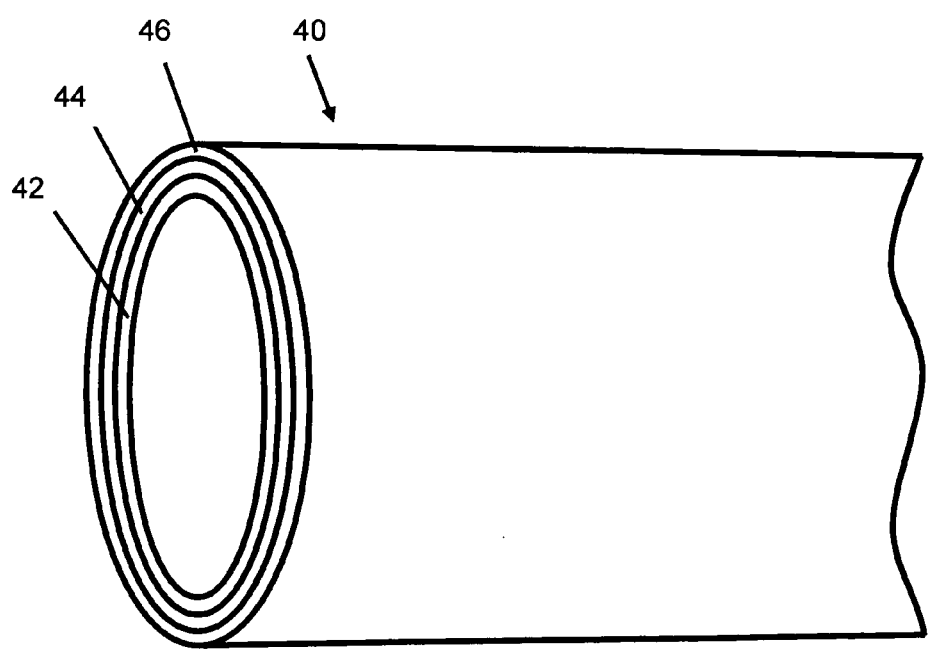
FIG. 4 is a schematic illustration of a tubular stent, in accordance with an embodiment of the present invention.

FIG. 4 illustrates a simplified tubular stent 40 in accordance with another embodiment of the present invention. The stent 40 comprises an tubular metallic substrate 42 coated with a lower polymeric layer 44 (which contains at least one polymer and at least one nitric oxide donor) and an upper polymeric layer 46 (which contains at least one polymer and an anti-restenotic agent). In general, tubular stents like that shown in FIG. 4 will include multiple openings such as slots or windows (not shown), which may be formed by any conventional process including, for example, laser cutting or chemical etching of thin metallic stock.

Numerous techniques are available for forming polymeric layers in accordance with the present invention. For example, where the polymer or polymers selected for use in the polymeric layers have thermoplastic characteristics, a variety of standard thermoplastic processing techniques can be used, including compression molding, injection molding, blow molding, vacuum forming and calendaring, as well as extrusion into sheets, tubes and other cross-sectional profiles of various lengths. For example, a polymeric layer can be provided by extrusion onto a pre-existing coated or uncoated medical device substrate. As another example, upper and lower polymeric coatings can be co-extruded onto a pre-existing medical device substrate, or they can be co-extruded along with the underlying medical device substrate. As yet another example, a polymeric layer can be provided by extrusion and attached to a medical device substrate.

If the therapeutic agents are stable at processing temperatures, then they can be combined with the polymers prior to thermoplastic processing. Alternatively, the therapeutic agents can be introduced subsequent to the formation of the polymeric layer using techniques such as imbibing, etc. (see below).

Solvent-based techniques are further techniques for forming polymeric layers in accordance with the present invention. Using these techniques, polymeric layers can be formed by first providing a solution that contains the polymer or polymers that will ultimately form the polymeric layers (as well as dissolved or dispersed therapeutic agents in many embodiments), followed by removal of the solvent. The solvent that is selected will typically contain one or more solvent species, which are generally selected based on their ability to dissolve the polymer or polymers that form the polymeric layers. They can also be selected based on other factors, including their ability to dissolve the therapeutic agent of interest, the drying rate, the surface tension, and so forth Generally several solvents will be tested to see which provides polymeric layers having the best characteristics.

Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

Where appropriate, such techniques can be repeated or combined to build up a polymeric layer to a desired thickness. The thickness of the polymeric layer can be varied in other ways as well. For example, in one preferred process, solvent spraying, coating thickness can be increased by modification of coating process parameters, including increasing spray flow rate, slowing the movement between the substrate to be coated and the spray nozzle, providing repeated passes and so forth.

In various embodiments, polymer solutions are applied over substrates to form the polymeric layers of the invention. For example, the substrates can correspond to all or portions of implantable or insertable medical devices, such as a stents. The substrates can also be, for example, templates such as molds from which the polymeric layers are is removed after solvent elimination and applied over a medical device substrate. In other embodiments, for example, solvent extrusion techniques, the polymeric layers are formed without the aid of a substrate and subsequently applied over a medical device substrate.

In some embodiments, the therapeutic agents of interest are added to the polymer solutions, for example, in dissolved or dispersed form, and hence co-established with the polymeric layers. In other embodiments, the therapeutic agents are dissolved within solvents, and the resulting solutions contacted (e.g., using one or more of the application techniques described above, such as dipping, spraying, etc.) with previously formed polymeric layers.

Where the polymeric layers are formed using solvent-based techniques, they are preferably dried after application to remove the solvent species. The polymeric layers typically further conform to any underlying surfaces during the drying process.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. An implantable or insertable medical device comprising: (a) a metallic substrate and (b) a coating comprising; (1) a lower polymeric layer provided over the substrate, said lower polymeric layer comprising a nitric oxide donor and a polymer; and (2) an upper polymeric layer provided over the lower polymer layer, said upper polymeric layer comprising a polymer and an anti-restenotic agent, wherein the medical device is adapted for implantation or insertion into the vasculature.

2. The implantable or insertable medical device of claim 1, wherein the metallic substrate is a stainless steel or a nickel-titanium alloy substrate.

3. The implantable or insertable medical device of claim 1, wherein the nitric oxide donor is selected from S-nitrosylated compounds and nonoate compounds.

4. The implantable or insertable medical device of claim 1, wherein the lower polymeric layer comprises a plurality of nitric oxide donors.

5. The implantable or insertable medical device of claim 1, wherein the lower polymeric layer completely covers the substrate.

6. The implantable or insertable medical device of claim 1, wherein the lower polymeric layer covers only a portion of the substrate.

7. The implantable or insertable medical device of claim 1, wherein the lower polymeric layer comprises a plurality of different polymers selected from homopolymers and copolymers.

8. The implantable or insertable medical device of claim 1, wherein the lower polymeric layer comprises a copolymer.

9. The implantable or insertable medical device of claim 8, wherein constitutional units forming the copolymer comprise olefin and vinyl aromatic monomers.

10. The implantable or insertable medical device of claim 1, wherein the lower polymeric layer comprises a block copolymer.

11. The implantable or insertable medical device of claim 1, wherein the anti-restenotic agent is selected from paclitaxel, rapamycin, and tacrolimus.

12. The implantable or insertable medical device of claim 1, wherein the anti-restenotic agent is paclitaxel.

13. The implantable or insertable medical device of claim 1, wherein the upper polymeric layer comprises a plurality of anti-restenotic agents.

14. The implantable or insertable medical device of claim 1, wherein the upper polymeric layer completely covers the lower polymeric layer.

15. The implantable or insertable medical device of claim 1, wherein the upper polymeric layer covers only a portion of the lower polymeric layer.

16. The implantable or insertable medical device of claim 1, wherein the upper polymeric layer comprises a plurality of different polymers selected from homopolymers and copolymers.

17. The implantable or insertable medical device of claim 1, wherein the upper polymeric layer comprises a copolymer.

18. The implantable or insertable medical device of claim 17, wherein the upper and lower polymeric layers comprise different polymers.

19. The implantable or insertable medical device of claim 1, wherein the upper polymeric layer comprises a block copolymer.

20. The implantable or insertable medical device of claim 1, wherein the upper and lower polymeric layers comprise different polymers.

21. The implantable or insertable medical device of claim 1, wherein the upper and lower polymeric layers comprise the same polymer.

22. The implantable or insertable medical device of claim 1, wherein the upper and lower polymeric layers comprise the same block copolymer.

23. The implantable or insertable medical device of claim 22, wherein said block copolymer comprises a polyolefin block.

24. The implantable or insertable medical device of claim 22, wherein said block copolymer comprises a poly(vinyl aromatic) block.

25. The implantable or insertable medical device of claim 22, wherein said block copolymer comprises a polyolefin block and a poly(vinyl aromatic) block.

26. The implantable or insertable medical device of claim 1, wherein the medical device is a stent.

27. The implantable or insertable medical device of claim 1, wherein the medical device is a stent, wherein the lower polymer layer comprises the nitric oxide donor and a block polymer comprising polyisobutylene and polystyrene blocks, and wherein the upper polymeric layer comprises paclitaxel and a block polymer comprising polyisobutylene and polystyrene blocks.

* * * * *